US008658200B2

(12) United States Patent
Mody et al.

(10) Patent No.: US 8,658,200 B2
(45) Date of Patent: *Feb. 25, 2014

(54) FLAVORING OF DRUG-CONTAINING CHEWING GUMS

(71) Applicant: McNeil-PPC, Inc., Skillman, NJ (US)

(72) Inventors: Seema Mody, Montville, NJ (US); Gregory Koll, Hillsborough, NJ (US)

(73) Assignee: McNeil-PPC, Inc., New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/662,517

(22) Filed: Oct. 28, 2012

(65) Prior Publication Data

US 2013/0052253 A1 Feb. 28, 2013

Related U.S. Application Data

(63) Continuation of application No. 11/131,561, filed on May 18, 2005, now Pat. No. 8,323,683.

(51) Int. Cl.
| A24B 15/16 | (2006.01) |
| A24B 15/00 | (2006.01) |
| A23G 4/00  | (2006.01) |
| A23G 4/08  | (2006.01) |

(52) U.S. Cl.
USPC ............ 424/440; 424/48; 424/439; 426/3; 426/4; 426/5; 426/103; 426/6; 131/270

(58) Field of Classification Search
USPC ........... 424/48, 440, 439; 426/3, 4, 5, 103, 6; 131/270
See application file for complete search history.

(56) References Cited

U.S. PATENT DOCUMENTS

| 3,845,217 | A | 10/1974 | Ferno et al. |
| 3,877,468 | A | 4/1975 | Lichtneckert et al. |
| 3,901,248 | A | 8/1975 | Lichtneckert et al. |
| 4,127,677 | A | 11/1978 | Fronczkowski et al. |
| 4,579,858 | A | 4/1986 | Ferno et al. |
| 4,627,977 | A | 12/1986 | Gaffar et al. |
| 4,753,790 | A | 6/1988 | Silva et al. |
| 4,828,845 | A | 5/1989 | Zamudio-Tena et al. |
| 4,933,190 | A | 6/1990 | Cherukuri et al. |
| 4,967,773 | A | 11/1990 | Shaw |
| 4,985,459 | A | 1/1991 | Sunshine et al. |
| 5,128,155 | A | 7/1992 | Song et al. |
| 5,135,761 | A | 8/1992 | Dave et al. |
| 5,167,242 | A | 12/1992 | Turner et al. |
| 5,286,502 | A | 2/1994 | Meyers |
| 5,433,960 | A | 7/1995 | Myers |
| 5,810,018 | A | 9/1998 | Monte et al. |
| 5,939,100 | A | 8/1999 | Albrechtsen et al. |
| 6,121,315 | A | 9/2000 | Nair et al. |
| 6,344,222 | B1 | 2/2002 | Cherukuri et al. |
| 6,440,396 | B1 | 8/2002 | McLaughlin |
| 6,627,234 | B1 | 9/2003 | Johnson et al. |
| 6,773,716 | B2 | 8/2004 | Ream et al. |
| 8,323,683 | B2 | 12/2012 | Mody et al. |
| 2004/0194793 | A1 | 10/2004 | Lindell et al. |

FOREIGN PATENT DOCUMENTS

| CN | 1348359 | 5/2002 |
| DE | 3241437 | 11/1982 |
| EP | 302024 | 7/1988 |
| JP | 7132051 | 5/1995 |
| WO | 93/12764 | 7/1993 |
| WO | 9706772 | 2/1997 |
| WO | 98/23165 | 6/1998 |
| WO | 00/13662 | 3/2000 |
| WO | 00/19977 | 4/2000 |
| WO | 0035298 | 6/2000 |
| WO | 0056281 | 9/2000 |
| WO | 02/102357 | 12/2002 |
| WO | 2004004478 | 1/2004 |
| WO | 2004049817 | 6/2004 |
| WO | 2004056363 | 7/2004 |
| ZA | 8702849 | 12/1986 |

OTHER PUBLICATIONS

Centers for Disease Control and Prevention. Cigarette smoking among adults—United States, 1995.
Russell et al., British Medical Journal, vol. 286, p. 683 (1983).
Jarvis et al., Brit. J. of Addiction, vol. 82, p. 983 (1987).
Rose, in Pharmacologic Treatment of Tobacco Dependence, (1986) pp. 158-166, Harvard Univ. Press.
Winter, Sorbitan Monooleate, Polysorbate 80, 1978, Consumer dictionary of food additives, Crown publishers Inc. Retrieved on Jan. 13, 2010, retrieved from Internet URL:, http://food.oregonstate.edu/glossary/s/sorbitanmonooleate.html.

*Primary Examiner* — Savitha Rao

(57) ABSTRACT

A chewing gum comprising at least one active pharmaceutical ingredient (API) with a core onto which is applied at least one inner polymer film coating and thereafter onto which is applied at least one outer hard coating. A preferred API is nicotine. Flavoring agents may be incorporated in the core, in the at least one inner polymer film coating and/or in the at least one outer hard coating. The gums formed exhibit a long lasting effect of flavoring agent(s) and result in the domination of flavoring agents in the coating(s) over flavoring agent(s) in the core, thereby (a) avoiding problems of chemical or pharmaceutical incompatibility between an API in the core and flavoring agent(s) in the coating(s) and (b) achieving an increased control of the release of the API and of non-active excipients.

20 Claims, No Drawings

FLAVORING OF DRUG-CONTAINING CHEWING GUMS

CROSS-REFERENCE TO RELATED APPLICATIONS

This application is a continuation of U.S. Pat. application Ser. No. 11/131,561, filed May 18, 2005, the entirety of which is hereby incorporated by reference as if fully set forth herein.

FIELD OF THE INVENTION

This invention relates to improved drug-containing gums, especially those containing nicotine.

BACKGROUND OF THE INVENTION

The present invention is useful for any active pharmaceutical ingredient (API), which may be administered with a chewing gum. A preferred API is nicotine. The following background mainly concerns nicotine as the API.

Tobacco dependence and reduction thereof is an important field. In recent years, with the recognition of the harmful effects of tobacco smoking, there have been numerous campaigns and programs by governmental agencies and various health groups and other interested organisations to disseminate information about the adverse health effects resulting from tobacco smoking. Moreover, and as a result of this recognition of the harmful effects, there have been many programs directed to attempts in reducing smoking incidence.

Nicotine is an organic compound and is the principal alkaloid of tobacco. Nicotine is the chief addictive ingredient in the tobacco used in cigarettes, cigars, snuff and the like. Nicotine is also an addictive drug, though, and smokers characteristically display a strong tendency to relapse after having successfully stopped smoking for a time. Nicotine is the worlds second most used drug, after caffeine from coffee and tea.

The main problem with tobacco smoking is its enormous implications on health. It is estimated that smoking related diseases cause some 3-4 million deaths per year. According to Centers for Disease Control and Prevention. Cigarette smoking among adults—United States, 1995, MMWR 1997; 46:1217-1220, around 500,000 persons in the USA die each year as a result of tobacco use. In fact, excessive smoking is now recognised as one of the major health problems throughout the world. This grim consequence of tobacco smoking has urged many medical associations and health authorities to take very strong actions against the use of tobacco.

Even though tobacco smoking is decreasing in many developed countries today it is hard to see how the societies could get rid of the world's second most used drug.

The most advantageous thing a heavy smoker can do is to reduce or preferably even stop smoking completely. Experience shows, however, that most smokers find this extremely difficult since, mostly, tobacco smoking results in a dependence disorder or craving. The WHO has in its International Classification of Disorders a diagnosis called Tobacco Dependence. Others like the American Psychiatric Association call the addiction Nicotine Dependence. It is generally accepted that these difficulties to stop smoking result from the fact those heavy smokers are dependent on nicotine. The most important risk factors are, however, substances that are formed during the combustion of tobacco, such as carbon monoxide, tar products, aldehydes, and hydrocyanic acid.

The effects of nicotine must be considered. The administration of nicotine can give satisfaction and the usual method is by smoking, either by smoking e.g. a cigarette, a cigar or a pipe. However, smoking has health hazards and it is therefore desirable to formulate an alternative way of administering nicotine in a pleasurable manner that can be used to facilitate withdrawal from smoking and/or used as a replacement for smoking.

When smoking a cigarette, nicotine is quickly absorbed into the smoker's blood and reaches the brain within around ten seconds after inhalation. The quick uptake of nicotine gives the consumer a rapid satisfaction or kick. The satisfaction, then, lasts during the smoking time of the cigarette and for a period of time thereafter. The poisonous, toxic, carcinogenic, and addictive nature of smoking has provided efforts for methods, compositions and devices, which help in breaking the habit of smoking cigarettes.

Nicotine is an addictive poisonous alkaloid $C_5H_4C_4H_7NCH_3$, derived from the tobacco plant. Nicotine is also used as an insecticide. Approximately 40 milligrams of nicotine is able to kill an adult (Merck Index).

Nicotine replacement products are important in the reduction of smoking. One way to reduce smoking is to provide nicotine in a form or manner other than by smoking and some products have been developed to fulfill this need. Nicotine containing formulations are currently the dominating treatments for tobacco dependence.

The successes in achieving reduction in the incidence of smoking have been relatively poor using presently known products. The present state of the art involves both behavioral approaches and pharmacological approaches. More than 80% of the tobacco smokers who initially quit smoking after using some behavioral or pharmacological ap proach. These persons who singly reduce smoking incidence generally relapse and return to the habit of smoking at their former rate of smoking within about a one year's period of time.

As an aid for those who are willing to stop smoking there are several ways and forms of nicotine replacement products available on the market; such as nicotine chewing gum. Several methods and means have been described for diminishing the desire of a subject to use tobacco, which comprises the step of administering to the subject nicotine or a derivative thereof as described in e.g., U.S. Pat. No. 5,810,018 (oral nicotine spray), U.S. Pat. No. 5,939,100 (nicotine containing microspheres) and U.S. Pat. No. 4,967,773 (nicotine containing lozenge).

Nicotine-containing nose drops have been reported (Russell et al., *British Medical Journal*, Vol. 286, p. 683 (1983); Jarvis et al., *Brit. J. of Addiction*, Vol. 82, p. 983 (1987)). Nose drops, however, are difficult to administer and are not convenient for use at work or in other public situations. Ways of administrating nicotine by way of delivering nicotine directly into the nasal cavity by spraying is known from U.S. Pat. No. 4,579,858; DE 32 41 437; and WO 93/127 64. There may, however, be local nasal irritation with use of nasal nicotine formulations. The difficulty in administration also results in unpredictability of the dose of nicotine administered.

The use of skin patches for transdermal administration of nicotine has been reported (Rose, in *Pharmacologic Treatment of Tobacco Dependence*, (1986) pp. 158-166, Harvard Univ. Press). Nicotine-containing skin patches that are in wide use today can cause local irritation and the absorption of nicotine is slow and affected by cutaneous blood flow.

Also, inhaling devices resembling a cigarette are known for uptake of nicotine vapours as suggested in U.S. Pat. No. 5,167,242. Said means and methods address the problems associated with addiction to nicotine.

Nicotine chewing gum is an important approach. One of the most successful approaches to date in reducing the incidence of smoking relies upon nicotine containing chewing gum that is designed to reduce smoking withdrawal symptoms. The reported success rate is approximately twice that of placebo.

Various approaches have been discussed for smoking reduction and/or cessation. One successful product that is used as a smoking substitute and/or as a smoking cessation aid and which is based on nicotine is the chewing gum Nicorette®. This product was one of the first nicotine replacement forms that was approved by the Food and Drug Administration (FDA) and is still one of the most used nicotine replacement products. Nicorette® chewing gum has been on the market in many countries for several years. In this chewing gum the nicotine is present in the form of a complex with an insoluble cation-exchanger (polacrilex) that is dispersed in a gum base. The nicotine is slowly released from the gum due to chewing and will reach similar plasma levels as when smoking a cigarette after about 30 minutes depending on the chewing technique, i.e., slow or active. Patents related to this product are, e.g., U.S. Pat. Nos. 3,877,468; 3,901,248; and 3,845,217.

WO 98/23165 discloses a chewing gum wherein nicotine may be in the coating. This concept may provide rapid release of the nicotine from the coated chewing gum, but not a sufficiently rapid buccal uptake of the nicotine. The fraction of the released nicotine that is not immediately absorbed will be flushed down in the gastrointestinal (G.I.) tract by the saliva, thereby possibly causing hiccups and other G.I. side effects. Once absorbed by the G.I. route, this swallowed nicotine will be subjected to first pass metabolism.

WO 00/13662 discloses a chewing gum for systemic, oral administration of an active whereby said active is administered by the chewing gum composition in a bi-phasic manner. The bi-phasic delivery is obtained by the gum matrix as such, not from any coating.

WO 00/19977 discloses a substantially moisture-free and possibly coated chewing gum for delivery of an active. The possible coating is not described as being buffered.

U.S. Pat. No. 5,433,960, assigned to William Wrigley Jr. Company, discloses a stick-shaped chewing gum being coated with an edible film, which comprises at least one active chewing gum agent such as sweetener, flavor, softener, slip agent, flavor enhancer, antioxidant and/or color. The coating may comprise a first layer as an edible film and a second layer comprising e.g. wax, fat, oil and/or a lipid derivative. It is not disclosed that the stick-shaped chewing gum with its coating may comprise any other drug than said active chewing gum agent.

WO 02/102357, assigned to Pharmacia AB, discloses a nicotine-containing chewing gum product comprising at least one coating, which coating is buffered.

U.S. Pat. No. 5,135,761, assigned to the Wrigley Company, discloses a coated chewing gum comprising a center, an emulsifier coating covering the center, and a hard panned coating covering the emulsifier coating. The emulsifier coating does not contain a polymer.

EP 302024A, assigned to Warner-Lambert, discloses a chewing gum comprising a first portion containing an L-aspartic acid derived sweetener, a second portion containing at least one flavoring agent, and a protective barrier film between the first and the second portions.

U.S. Pat. No. 4,828,845, assigned to Warner-Lambert, discloses a process for producing a coated chewing gum, whereby at least three coating solutions are applied one after the other by spraying on to a chewing gum core.

ZA 8702849, assigned to Warner-Lambert, discloses a chewing gum with a core and at least two coating solutions, both solutions comprising sorbitol and film-forming agents, such as hydroxypropylmethyl cellulose ("HPMC").

U.S. Pat. No. 4,933,190, assigned to Warner-Lambert, discloses a chewing gum capable of releasing increased amounts of sweetness, which has a first inner coating comprising polyvinyl acetate and a second outer coating comprising a hydrophilic polymer.

None of the above references disclose any solution to the combined problems of obtaining a long lasting effect of flavoring agent(s), domination of flavoring agents in the coating(s) over flavoring agent(s) in the core, avoiding problems of chemical or pharmaceutical incompatibility between a drug in the core and flavoring agent(s) in the coating(s), and/or increasing the control of the release of the drug.

SUMMARY OF THE INVENTION

This invention relates to drug-containing chewing gums, comprising a gum core over which is applied at least one inner polymer film coating and whereon is applied at least one outer hard coating over the inner polymer film coating. Flavoring agents may be incorporated in the core, in the at least one inner polymer film coating and/or in the at least one outer hard coating. A preferred drug is nicotine. Advantages of the invention include long lasting effect of flavoring agent(s), domination of flavoring agents in the coating(s) over flavoring agent(s) in the core, the avoidance of problems of chemical or pharmaceutical incompatibility between a drug in the core and flavoring agent(s) in the coating(s), and increased control of the release of the drug and of non-active excipients.

The present invention also provides, as particular embodiments, new and improved products as a coated chewing gum containing an active pharmaceutical ingredient (API) and providing for obtaining of a long lasting effect of flavoring agent(s), domination of flavoring agents in the coating(s) over flavoring agent(s) in the core, avoiding problems of chemical or pharmaceutical incompatibility between an API in the core and flavoring agent(s) in the coating(s), and/or increasing the control of the release of the drug.

A preferred API is nicotine in any form.

DETAILED DESCRIPTION OF THE INVENTION

With reference to this invention, the term "chewing gum" means all chewable gum products. The term "API" intends to mean active pharmaceutical ingredient. The term "nicotine" intends to mean nicotine in any form, be it the free base form, a salt, a complex or any other form.

For flavored API-containing chewing gums the invention provides a solution to the combined problem of obtaining a long lasting effect of the flavoring agent(s), obtaining domination of flavoring agents in the coating(s) over flavoring agent(s) in the core, avoiding problems of chemical or pharmaceutical incompatibility between an API in the core and flavoring agent(s) in the coating(s), and/or increasing the control of the release of the drug. Known techniques for flavoring chewing gums imply that flavoring agents are added to a gum core and optionally to a hard coating on the core. Anyhow, such flavoring does not solve the preceding problem.

According to the present invention said combined problem is solved by providing a chewing gum core with at least one inner polymer film coating and at least one outer hard coating, whereby the flavoring agent(s) is/are added to at least the inner polymer film coating. The API may be in the core and/or in one or more of the coatings. For a nicotinecontaining chewing gum the nicotine is preferably in the core and in an at least one inner polymer film coating for providing quick nicotine release from the film and slow nicotine release from the core. For a dextromethorphan-containing chewing gum the dextromethorphan is preferably only in an at least one inner polymer film coating to avoid entrapment of dextromethorphan in the core and for quick release from the film.

The API may be any API suitable for delivery with a chewing gum. The most preferred API is nicotine. Other suitable APIs are preferably selected among the below listed compounds.

Teeth whitening actives may be included in one or both coatings of the present invention. The actives suitable for whitening are selected from the group consisting of oxalates, peroxides, metal chlorites, perforates, percarbonates, peroxyacids, and mixtures thereof. Suitable peroxide compounds include hydrogen peroxide, calcium peroxide, sodium peroxide, carbamide peroxide, urea peroxide, sodium percarbonate and mixtures thereof. Optionally, the peroxide is hydrogen peroxide. Suitable metal chlorites include calcium chlorite, barium chlorite, magnesium chlorite, lithium chlorite, sodium chlorite and potassium chlorite. Additional whitening actives may be hypochlorite and chlorine dioxide. A preferred chlorite is sodium chlorite. The effectiveness of whitening actives can, optionally, be enhanced by means of a catalyst, i.e. a two-component peroxidecatalyst system. Useful whitening agent catalysts or catalytic agents can be found in U.S. Pat. No. 6,440,396 to McLaughlin, herein incorporated by reference in its entirety as to the description of whitening agents and systems.

When incorporating peroxide actives, the coating compositions of the present invention can, optionally, contain peroxide active stabilizers. Peroxide active stabilizers suitable for use herein include, but are not limited to, polyethylene glycols such as PEG 40 or PEG 600; zinc salts such as zinc citrate; polyoxyalkylene block-polymers (e.g. Pluronics); aminocarboxylic acids or salts thereof; glycerols; dyes such as Blue #1 or Green #3; phosphates such as phosphoric acid, sodium phosphate or sodium acid pyrophosphate; stannous salts such as stannous chloride; sodium stannate; citric acid; etidronic acid; carbomers or carboxypolymethylenes such as those of the Carbopol® series, butylated hydroxytoluene (BHT), ethylenediaminetetraacetic acid (EDTA) and mixtures thereof.

Anti-tartar agents useful herein include phosphates. Phosphates include pyrophosphates, polyphosphates, polyphosphonates and mixtures thereof. Pyrophosphates are among the best known phosphates for use in dental care products. Pyrophosphate ions delivered to the teeth derive from pyrophosphate salts. The pyrophosphate salts useful in the present compositions include the dialkali metal pyrophosphate salts, tetra-alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their non-hydrated as well as hydrated forms are preferred. Anticalculus phosphates include potassium and sodium pyrophosphates; sodium tripolyphosphate; diphosphonates, such as ethane-1-hydroxy-1,1-diphosphonate; 1-azacycloheptane-1,1-diphosphonate; and linear alkyl diphosphonates; linear carboxylic acids and sodium and zinc citrate.

Agents that may be used in place of or in combination with the above pyrophosphate salt include materials such as synthetic anionic polymers including polyacrylates and copolymers of maleic anhydride or acid and methyl vinyl ether, e.g. Gantrez, as described, for example, in U.S. Pat. No. 4,627,977, to Gaffar et al. herein incorporated by reference in its entirety as to the description of such agents, as well as e.g. polyamino propane sulfonic acid (AMPS), zinc citrate trihydrate, polyphosphates, e.g. tripolyphosphate and hexametaphosphate, diphosphonates, e.g. EHDP and AMP, polypeptides, such as polyaspartic and polyglutamic acids, and mixtures thereof.

Antimicrobial agents can also be present in the coating compositions of the present invention as oral agents and/or systemic actives. Such agents may include, but are not limited to, 5-chloro-2-(2,4-dichlorophenoxy)-phenol, commonly referred to as triclosan, chlorhexidine, alexidine, hexetidine, sanguinarine, benzalkonium chloride, salicylamide, domiphen bromide, cetylpyridium chloride (CPC), tetradecyl pyridinium chloride (TPC); N-tetradecyl-4-ethyl pyridinium chloride (TDEPC); octenidine; delmopinol, octapinol, and other piperidino derivatives, niacin preparations; zinc/stannous ion agents; antibiotics such as AUGMENTIN, amoxycillin, tetracycline, doxycyline, minocycline, and metronidazole; and analogs, derivatives and salts of the above antimicrobial agents and mixtures thereof.

Anti-inflammatory agents can also be present in the coating compositions of the present invention as oral agents and/or systemic actives. Such agents may include, but are not limited to, non-steroidal anti-inflammatory agents or NSAIDs, such as propionic acid derivatives; acetic acid derivatives; fenamic acid derivatives; biphenylcarboxylic acid derivatives; and oxicams. All of these NSAIDs are fully described in U.S. Pat. No. 4,985,459 to Sunshine et al., incorporated by reference herein in its entirety as to the description of such NSAIDs. Examples of useful NSAIDs include acetylsalicylic acid, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen, bucloxic acid and mixtures thereof. Also useful are the steroidal anti-inflammatory drugs such as hydrocortisone and the like, and COX-2 inhibitors such as meloxicam, celecoxib, rofecoxib, valdecoxib, etoricoxib or mixtures thereof. Mixtures of any of the above anti-inflammatories may be used.

Other materials that can be used with the present invention include commonly known mouth and throat products. These products include, but are not limited to, upper respiratory agents such as phenylephrine, diphenhydramine, dextromethorphan, bromhexine and chlorpheniramine, gastrointestinal agents such as famotidine, loperamide and simethicone, anti-fungals such as miconazole nitrate, antibiotics and analgesics such as ketoprofen and fluributprofen.

At least the inner polymer coating comprises a flavoring agent. Also the outer hard coating may comprise a flavoring agent.

One or more of the coatings may comprise sweetening agents and/or further additives as described below.

One particular embodiment comprises embedding the flavoring agent in the polymer coating to prolong the flavoring sensation.

In order to reduce manufacturing costs and in order to facilitate product approval for similar chewing gums by health authorities it is often desirable to use the same core with differently flavored coatings. Thereby the flavor of the core needs to be dominated by the flavor of the coating(s). This effect is obtained by the present invention where the flavor of the at least one inner polymer coating may dominate over the flavor of the core. An example of such domination is when a fruit flavor in the at least one inner polymer coating dominates over a mint flavor of the core. The mechanism behind this flavor domination is that the flavor in the polymer coating has a slow release therefrom. Further, upon chewing, part of the polymer coating gets embedded in the core, from where the polymer film flavor is subsequently slowly released. Polymer coating also allows for addition of a large percentage of flavor as compared to a hard coating.

An outer hard coating may cover the polymer film coating whereby an objectionable taste of an API or of another excipient in the polymer film coating which directly affects the oral mucosa is avoided.

By keeping the flavoring agent in the polymer coating, and optionally also in the hard coating, the flavoring agent is held isolated from an API in the core, thus avoiding the possible problem of chemical or pharmaceutical incompatibility between the API and the flavoring agent. An example of such incompatibility is nicotine in direct contact with cinnamon flavor, whereby cinnamon aldehydes in the cinnamon flavor degrade the nicotine.

Polymers suitable for use in the at least one inner polymer coating are preferably selected from, but not limited to, the group consisting of hydroxypropyl cellulose, hydroxypropylmethyl cellulose, hydroxyethyl cellulose, polyvinyl pyrrolidone, carboxymethyl cellulose, polyvinyl alcohol, sodium alginate, polyethylene glycol, pullulan, tragacanth gum, guar gum, acacia gum, arabic gum, polyacrylic acid, methyl-methacrylate copolymer, carboxyvinyl polymer, amylose, high amylose starch, hydroxypropylated high amylose starch, dextrin, pectin, chitin, chitosan, gelatin, zein, gluten, soy protein isolate, whey protein-isolate, casein and mixtures thereof. Suitable polymers also include water-insoluble polymers selected from the group consisting of hydrogenated vegetable oils, hydrogenated caster oil, polyvinyl chloride, shellac, polyurethane, cellulose derivatives, gum rosins, wood rosens, waxes, acrylate and methacrylate polymers, copolymers of acrylic and methacrylic acid esters and mixtures thereof.

The amount of gum base in the coated chewing gum according to the invention is about 15-80% by weight of the total gum core, and preferably at least about 40% by weight. The amount of gum base employed for the most desirable slow release of nicotine is usually in the higher ranges when nicotine is employed per se or when an absorbed form is used.

The gum base may be of any conventional nature known in the art. For example it may comprise a gum base of natural or synthetic origin readily available from a commercial source. Natural gum bases include e.g. chicle, jelutong-, lechi de caspi-, soh-, siak-, katiau-, sorwa-, balata-, pendare-, malaya-, and peach gums, natural cautchouc and natural resins such as dammar and mastix. Synthetic gum bases are a mixture of:

elastomers (polymers, masticating substances),
plasticizer (resin, elastomers, solvent, hydrophobic resin),
filler (texturizer, water-insoluble adjuvant),
softener (fat),
emulsifier,
wax,
antioxidant, and
anti-tacking agents (vinyl polymer, hydrophilic resin).

Other examples of gum bases are gums including agar, alginate, arabic gum, carob gum, carrageenan, ghatti gum, guar gum, karaya gum, pectin, tragacanth gum, locust beam gum, gellan gum and xanthan gum.

Examples of gelling agents comprise gum arabic, starch, gelatine, agar, and pectin.

When nicotine in any form is incorporated in the chewing gum mass in accordance with the present invention, it is possible to employ a wide variety of chewing gum compositions and amounts of the chewing gum base. Different chewing gum products may be composed depending on the consumer's preference and the purpose of use, in respect of the nicotine level, nicotine distribution and other additives.

According to one aspect of the invention, the chewing gum may comprise nicotine in any form. The nicotine may act as a stimulant to e.g. obtain a rapid reduction of the urge to smoke or to use tobacco. More particularly, the nicotine should be in a saliva soluble form to facilitate the release of the agent into the saliva in the oral cavity and, further, the subsequent uptake of the nicotine from the saliva in the oral cavity into the systemic circulation of the subject.

With nicotine it is intended to include nicotine, 3-(1-methyl-2-pyrrolidinyl)-pyridine, with its base form, including synthetic nicotine as well as nicotine extracts from tobacco plants, or parts thereof, such as the genus Nicotiana alone or in combination or pharmaceutically acceptable salts.

Preferred embodiments incorporate nicotine as
(a) the free base form;
(b) a water-soluble pharmaceutically acceptable salt, either per se or adsorbed on an adsorbent;
(c) a complex with a cation exchanger;
(d) mixtures of any of (a)-(c);
(e) an inclusion complex, such as a cyclodextrin complex, e.g. β-cyclodextrin, or nicotine in any non-covalent binding;
(f) nicotine bound to zeolites;
(g) nicotine bound to cellulose or starch microspheres; and
(h) mixtures of any of the foregoing.

Also, any other suitable pharmaceutically acceptable form may also be employed.

As noted above, numerous nicotine salts are known, and may be used. Particular examples of suitable salts include those presented in Table 1, such as preferably the tartrate, hydrogen tartrate, citrate, malate, and/or hydrochloride.

TABLE 1

Possible acids used for nicotine salt formation

| Acid | Molar ratio* of acid:nicotine |
|---|---|
| Formic | 2:1 |
| Acetic | 3:1 |
| Propionic | 3:1 |
| Butyric | 3:1 |
| 2-Methylbutyric | 3:1 |
| 3-Methylbutyric | 3:1 |
| Valeric | 3:1 |
| Lauric | 3:1 |
| Palmitic | 3:1 |
| Tartaric | 2:1 |
| Citric | 2:1 |
| Malic | 2:1 |
| Oxalic | 2:1 |
| Benzoic | 1:1 |
| Gentisic | 1:1 |
| Gallic | 1:1 |
| Phenylacetic | 3:1 |
| Salicylic | 1:1 |
| Phthalic | 1:1 |
| Picric | 2:1 |
| Sulfosalicylic | 1:1 |
| Tannic | 1:5 |
| Pectic | 1:3 |
| Alginic | 1:2 |
| Hydrochloric | 2:1 |
| Chloroplatinic | 1:1 |
| Silicotungstic | 1:1 |
| Pyruvic | 2:1 |
| Glutamic | 1:1 |
| Aspartic | 1:1 |

*recommended upon production

As noted above the nicotine may be present in the chewing gum in a complex with a cation exchanger. Suitable cation exchangers are listed below Table 2 and are further disclosed in U.S. Pat. No. 3,845,217, hereby incorporated by reference herein as to the description of such cation exchangers. Preferred are nicotine cation exchangers of polyacrylates, such as the AMBERLITE products from Rohm & Haas in Table 2.

TABLE 2

Representative cation exchangers

| Name | Manufacturer |
| --- | --- |
| Amberlite IRC 50 | Rohm & Haas |
| Amberlite IRP 64 | Rohm & Haas |
| Amberlite IRP 64M | Rohm & Haas |
| BIO-REX 70 | BIO-RAD Lab. |
| Amberlite IR 118 | Rohm & Haas |
| Amberlite IRP 69 | Rohm & Haas |
| Amberlite IRP 69M | Rohm & Haas |
| BIO-REX 40 | BIO-RAD Lab. |
| Amberlite IR 120 | Rohm & Haas |
| Dowex 50 | Dow Chemical |
| Dowex 50W | Dow Chemical |
| Duolite C 25 | Chemical Process Co |
| Lewatit S 100 | Farbenfabriken Bayer |
| Ionac C 240 | Ionac Chem. |
| Wofatit KP S 200 | I.G. Farben Wolfen |
| Amberlyst 15 | Rohm & Haas |
| Duolite C-3 | Chemical Process |
| Duolite C-10 | Chemical Process |
| Lewatit KS | Farbenfabriken Bayer. |
| Zerolit 215 | The Permutit Co. |
| Duolite ES-62 | Chemical Process |
| BIO-REX 63 | BIO-RAD Lab. |
| Duolite ES-63 | Chemical Process |
| Duolite ES-65 | Chemical Process |
| Ohelex 100 | BIO-RAD Lab. |
| Dow Chelating Resin A-1 | Dow Chemical Company |
| Purolite C115HMR | Purolite International Ltd. |
| CM Sephadex C-25 | Pharmacia Fine Chemicals |
| SE Sephadex C-25 | Pharmacia Fine Chemicals |

A coated chewing gum according to the present invention may comprise one or more further non-active excipients or additional active ingredients, preferably selected from the compounds listed herein.

One or more fluoride ion sources may be incorporated into the coating compositions as anticaries agents. Fluoride ions may be included for this purpose. Detailed examples of such fluoride ion sources can be found in U.S. Pat. No. 6,121,315 to Nair et al., herein incorporated by reference as to the description of such fluoride ion sources.

Also useful herein are tooth desensitizing agents. Tooth desensitizing agents that may be used in the present invention include potassium nitrate, citric acid, citric acid salts, strontium chloride, and the like, as well as other desensitizing agents known in the art. One particular embodiment includes a desensitizing agent in combination with a tooth whitening agent. The amount of desensitizing agent included within the dental whitening compositions of the present invention may vary according to the concentration of the potassium nitrates, the desired strength and intended treatment times. Accordingly, if included at all, the other desensitizing agents will preferably be included in an amount in a range from about 0.1% to about 10% by weight of the dental desensitizing composition, more preferably in a range from about 1 to about 7% by weight of the wet film composition.

An individual enzyme or a combination of several compatible enzymes can also be included in the chewing gum composition of the present invention.

Antioxidants are generally recognized as useful in compositions such as those of the present invention. Antioxidants that may be included in the coating compositions of the present invention include, but are not limited to, Vitamin E, ascorbic acid, uric acid, carotenoids, Vitamin A, flavonoids and polyphenols, herbal antioxidants, melatonin, aminoindoles, lipoic acids and mixtures thereof.

It may be desirable to add pH adjusting agents, or buffers, such as sodium bicarbonate, sodium phosphate, sodium hydroxide, ammonium hydroxide, sodium stannate, citric acid, hydrochloric acid, sodium citrate, and combinations thereof to the core and/or to any of the coatings. The pH adjusting agents are added in sufficient amounts so as to adjust the pH of oral cavity to a suitable value, e.g. from about 4.5 to about 11, preferably from about 5.5 to about 8.5.

EXAMPLES

The following Examples are offered as illustrative of the invention and are not to be construed as limitations thereon. In the Examples and elsewhere in the description of the invention, chemical symbols and terminology have their usual and customary meanings. The term "set" is an inclusive term used to mean a single or more than one ingredient of the type described. In the Examples as elsewhere in this application the proportions of the components are in weight percents according to the standard described, or if no standard is described of the total weight of the composition.

The Examples may be modified according to suitable and conventional manufacturing methods known in the art. The methods of the Examples may be modified e.g. in accordance with the methods disclosed in WO 02/102357, herein incorporated by reference as to the description of manufacturing methods.

Example 1

Nicotine-containing Chewing Gums

Chewing gums according to the present invention, preferably each containing 2 mg or 4 mg nicotine calculated as the free base are manufactured according to the below process. The number of gums being manufactured per batch will depend on the equipment used.

The following steps are carried out:
1. Chewing gum base is loaded into a pre-heated mixer and agitated therein.
2. A first set of flavoring agent(s), sweetener(s), pH regulating agents and nicotine resin complex are added and mixed therein until a homogenous distribution of the ingredients is obtained.
3. The chewing gum mass is extruded, conditioned and rolled and scored to form chewing gum sheets.
4. The chewing gum sheets are conditioned and then broken into individual chewing gum cores.
5. A polymer-containing coating solution, e.g. comprising HPMC, is prepared. A second set of sweetener(s) and flavoring agent(s) are added to the solution.
6. The chewing gum cores are loaded into coating pans where they are sprayed with the coating solution from Step 5.
7. A hard coating solution comprising a third set of sweetener(s) and, optionally, a third set of flavoring agent(s) is prepared.
8. The coated gum cores are again loaded into coating pans. The coating solution from Step 7 is sprayed in cycles onto the coated gum cores.

9. Optionally wax is sprayed onto the coated gum cores in order to provide a glossy finish.

In Step 6 the coating solution is applied using a spray coater. For example, gum cores are film coated in a controlled atmosphere inside a perforated rotating drum. Angled baffles are fitted into the drum and air flow inside the drum provides means of mixing the gum cores bed. As a result, the gum cores are lifted and turned from the sides into the center of the drum, exposing each gum core surface to an even amount of deposited/sprayed film forming agent to produce a coating. The liquid spray coating is then dried onto the gum core by air drawn through the tablet bed from an inlet fan. The air flow is regulated for temperature and volume to provide controlled drying and extracting rates, and at the same time, maintaining the drum pressure slightly negative relative to the room in order to provide a completely isolated process atmosphere for the operator.

Suitable coating equipment may include spray guns, coating pan, polishing pans, solution tanks, blenders and mixers, homogenizers, mills, peristaltic pumps, fans, steam jackets, exhaust and heating pipes, scales and filters. In particular, any commercial spray coater may be used to apply the coating. Examples of useful coaters are Vector High Coaters manufactured by Vector Corporation and Accela-Coat manufactured by Thomas Engineering. Equipment variables which one skilled in the art can manipulate to provide a coating based on HPMC or HPC, include inlet temperature, outlet temperature, air flow, speed of rotation of the coating pan, and the rate at which the coating formulation is pumped to the coater. It is important that the inlet and outlet temperatures be controlled so that they are high enough to efficiently dry the coating to prevent the tumbling action of the already-coated tablets from damaging the newly-applied coating before more coating is applied to the same tablets.

A chewing gum comprising 2 mg nicotine being manufactured in accordance with the above process may have the following composition:

the gum core: 314 mg xylitol, 20 mg sodium carbonate anhydrous, 10 mg sodium hydrogen carbonate, 1 mg magnesium oxide light, 2 mg acesulfame potassium, 11 mg nicotine resin complex 20%, 560 mg chewing gum base, 2 mg levomenthol and 30 mg peppermint oil;

the polymer coating: 11.5 mg Methocel K3 Prem LV (HPMC 2208, 3 cps), 5 mg sucralose NF, 0.5 mg Polysorbate 80 NF/EP, 10 mg cinnamon flavor and 3 mg Indian fire flavor;

the hard coating: 270 mg xylitol, 6 mg acacia spray-dried, 5 mg titanium dioxide, 6.15 mg cinnamon flavor, 1.85 mg Indian fire flavor and 1 mg carnauba wax.

Example 2

Alternative Nicotine-containing Chewing Gums

Several modifications to the process described in Example 1 and the product resulting therefrom are possible. For example:

(a) Instead of HPMC, one can use hydroxy propyl cellulose (HPC), such as Klucel EF from Aqualon.

(b) A plasticizer may be mixed into the polymer film in order to improve flexibility of the film. Examples of suitable plasticizers include, but are not limited to, citric acid alkyl esters, glycerol esters such as glycerol monooleate and glycerol monostearate, phthalic acid alkyl esters, sebacic acid alkyl esters, sucrose esters, sorbitan esters, acetylated monoglycerides, glycerols, fatty acid esters, glycols, propylene glycol, and polyethylene glycols 200 to 12,000 and mixtures thereof. Specific plasticizers include, but are not limited to, lauric acid, sucrose, sorbitol, triethyl citrate, acetyl triethyl citrate, triacetin (glyceryl triacetate), poloxamers, alkyl aryl phosphates, diethyl phthalate, mono- and di-glycerides of edible fats or oils supplied by Lonza Inc., tributyl citrate, dibutyl phthalate, dibutyl sebacate, polysorbate, Carbowax® series of polyethylene glycols (Union Carbide Corporation) and mixtures thereof. Preferred plasticizers include polyethylene glycol 400 (PEG 400) in amounts ranging from about 0 to about 10% by weight, preferably about 0 to about 3% by weight.

(c) Particular embodiments include those where the level of polymer coating applied to the gum cores is preferably between about 0.5% and about 20% by weight of the uncoated gum cores, more preferably between about 2% and about 3.5% by weight of the uncoated gum cores. This level of coating provides an elegant and serviceable coating. To apply a heavier coating to the gum cores would not be economical, and it might adversely affect active release or other properties. Too light a coating would not provide optimal properties normally expected from a coating.

(d) In general, an effective amount of auxiliary sweetener is utilized to provide the level of sweetness desired for a particular composition, and this amount will vary with the sweetener selected. This amount will normally be from about 0.01% to about 30% by weight of the polymer film coating when using sucralose and, most preferably, in amount of from about 10% to about 20% by weight. These amounts may be used to achieve a desired level of sweetness independent from the flavor level achieved from any optional flavor oils used.

(e) The polymer used in the polymer coating is preferably water-soluble and is present therein in an amount up to about 99% by weight, preferably up to about 80% by weight, more preferably up to about 50% by weight, and most preferably up to about 40% by weight of the polymer coating.

(f) In Step 7 may be added non-ionic emulsifiers such as mono- and diglycerides of fatty acids, ethylene glycol fatty acid esters, propylene glycol fatty acid esters, glycerol monostearate, and polyoxyethylene sorbitol esters. Specific examples are Atmos 300 and Polysorbate 80. Said emulsifiers can be added in amounts ranging from about 0.5% to about 15% by weight, preferably from about 1% to about 5% by weight of the polymer film coating.

(g) The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. In general, in the inner polymer film amounts of from about 0.1% to about 60% by weight are useable with amounts of from about 2% to about 50% by weight being preferred and amounts from about 30% to about 50% by weight being more preferred.

(h) Further additives as stated above may be incorporated in the chewing gums.

A typical inner polymer film coating comprises the hydroxypropylmethyl cellulose Methocel K3, the surfactant Polysorbate 80, the sweetener Sucralose and flavor. The inner polymer film coating may additionally comprise the hydroxypropyl cellulose Klucel EF. A typical outer hard coating comprises the sweetener Xylitol, the film former Gum Arabic, the colorant titanium dioxide, flavors and Carnauba Wax.

Example 3

Chewing Gums Comprising other APIs than Nicotine

Chewing gums according to the present invention comprising API's other than nicotine may be manufactured according to Example 1 or Example 2.

Example 3A

Chewing Gums Comprising Dextromethorphan

A dextromethorphan-containing chewing gum, eg having a gum core comprising 10 mg of the AIP dextromethorphan, may have an inner polymer film comprising the hydroxy propyl methyl cellulose Methocel K3, the surfactant Polysorbate 80, the sweetener Sucralose, the AIP dextromethorphan and Mint Flavor. The outer hard coating may comprise the sweetener Xylitol, the film former Gum Arabic, the colorant Titanium Dioxide, Mint Flavor and Carnauba Wax.

Example 3B

Chewing Gums for Oral Care

A chewing gum for oral care may have an inner polymer film comprising the hydroxy propyl methyl cellulose Methocel K3; the surfactant Polysorbate 80; the sweetener Sucralose; the AIP's menthol, Thymol, Eucalyptol and methyl salicylate; and a flavoring such as peppermint flavor. The outer hard coating may comprise the sweetener Xylitol, the film former Gum Arabic, the colorant titanium dioxide, peppermint flavor and Carnauba Wax.

What is claimed is:

1. A chewing gum comprising:
   (a) a core comprising chewing gum base, nicotine in any form, a first flavoring agent, a first sweetener and at least one pH regulating agent;
   (b) an inner polymer coating on the core, a second flavoring agent in an amount from 30% to 50% by weight of said inner polymer coating and a second sweetener wherein the amount of inner polymer coating is about 0.5% to about 20% by weight of the core; and
   (c) an outer hard coating on the inner polymer coating whereby the flavor perceived upon chewing of the chewing gum predominantly is the flavor provided by said at least one second flavoring agent.

2. The chewing gum according to claim 1, wherein said inner polymer coating comprises water soluble natural or synthetic polymer selected from the group consisting of hydroxypropyl cellulose, hydroxypropylmethyl cellulose, hydroxyethyl cellulose, polyvinyl pyrrolidone, carboxymethyl cellulose, polyvinyl alcohol, sodium alginate, polyethylene glycol, pullulan, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, gelatin, zein, gluten, soy protein isolate, whey protein-isolate, casein and mixtures thereof.

3. The chewing gum according to claim 1, wherein said inner polymer coating comprises a water-insoluble polymer selected from the group consisting of hydrogenated vegetable oils, hydrogenated castor oil, polyvinyl chloride, shellac, polyure-thane, cellulose derivatives, gum rosins, wood rosens, waxes, acrylate and methacrylate polymers, copolymers of acrylic and methacrylic acid esters and mixtures thereof.

4. The chewing gum according to claim 2, wherein said inner polymer coating further comprises a plasticizer.

5. The chewing gum according to claim 1, wherein said inner polymer film coating and said outer hard coating are devoid of any active pharmaceutical ingredient.

6. The chewing gum according to claim 1, wherein said inner polymer film coating further comprises one or more ingredients selected from the group consisting of: fluoride ion sources, tooth desensitizing agents, enzymes, antioxidants, pH adjusting agents, and mixtures of the foregoing.

7. The chewing gum according to claim 1, wherein said first flavoring agent is mint and said second flavoring agent is selected from the group consisting of citrus, cinnamon, berry or mixed fruit.

8. The chewing gum according to claim 1, wherein said inner polymer coating further comprises a plasticizer.

9. The chewing gum according to claim 8, wherein said plasticizer comprises polysorbate.

10. A chewing gum comprising:
    (a) a core comprising chewing gum base, nicotine in any form and a first flavoring agent;
    (b) an inner polymer coating on the core and a second flavoring agent in an amount from 30% to 50% by weight of said inner polymer coating wherein the amount of inner polymer coating is about 0.5% to about 20% by weight of the core; and
    (c) an outer hard coating on the inner polymer coating whereby the flavor perceived upon chewing of the chewing gum predominantly is the flavor provided by said at least one second flavoring agent.

11. The chewing gum according to claim 10, wherein said core further comprises a sweetener.

12. The chewing gum according to claim 10, wherein said inner polymer coating further comprises a sweetener.

13. The chewing gum according to claim 10, wherein said outer polymer coating further comprises a sweetener.

14. The chewing gum according to claim 10, wherein said inner polymer film coating and said outer hard coating are devoid of any active pharmaceutical ingredient.

15. The chewing gum according to claim 10, wherein said inner polymer film coating further comprises one or more ingredients selected from the group consisting of: fluoride ion sources, tooth desensitizing agents, enzymes, antioxidants, pH adjusting agents, and mixtures of the foregoing.

16. The chewing gum according to claim 10, wherein said first flavoring agent is mint and said second flavoring agent is selected from the group consisting of citrus, cinnamon, berry or mixed fruit.

17. The chewing gum according to claim 10, wherein said inner polymer coating further comprises a plasticizer.

18. The chewing gum according to claim 17, wherein said plasticizer comprises polysorbate.

19. The chewing gum according to claim 10, wherein said inner polymer coating comprises water soluble natural or synthetic polymer selected from the group consisting of hydroxypropyl cellulose, hydroxypropylmethyl cellulose, hydroxyethyl cellulose, polyvinyl pyrrolidone, carboxymethyl cellulose, polyvinyl alcohol, sodium alginate, polyethylene glycol, pullulan, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, gelatin, zein, gluten, soy protein isolate, whey protein-isolate, casein and mixtures thereof.

20. The chewing gum according to claim 4, wherein said plasticizer comprises polysorbate.

\* \* \* \* \*